(12) United States Patent
Thirumoorthy et al.

(10) Patent No.: US 12,083,295 B2
(45) Date of Patent: Sep. 10, 2024

(54) CATHETER ASSEMBLY HAVING A SIDE PORT VALVE

(71) Applicant: Becton, Dickinson and Company, Franklin Lakes, NJ (US)

(72) Inventors: Sankaranarayanan Thirumoorthy, Tamil Nadu (IN); Mukilan Balamurugan, Tamil Nadu (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/870,637

(22) Filed: Jul. 21, 2022

(65) Prior Publication Data

US 2022/0355081 A1 Nov. 10, 2022

Related U.S. Application Data

(63) Continuation of application No. 16/878,121, filed on May 19, 2020, now Pat. No. 11,420,025.

(60) Provisional application No. 62/860,537, filed on Jun. 12, 2019.

(51) Int. Cl.
*A61M 25/06* (2006.01)
*A61M 39/10* (2006.01)
*A61M 39/22* (2006.01)
*A61M 25/01* (2006.01)

(52) U.S. Cl.
CPC .... *A61M 25/0631* (2013.01); *A61M 25/0606* (2013.01); *A61M 25/0643* (2013.01); *A61M 39/10* (2013.01); *A61M 39/22* (2013.01); *A61M 2025/018* (2013.01); *A61M 2039/1077* (2013.01)

(58) Field of Classification Search
CPC .......... A61M 25/0631; A61M 25/0606; A61M 25/0643; A61M 39/10; A61M 39/22
USPC .......................................................... 604/523
See application file for complete search history.

(56) References Cited

U.S. PATENT DOCUMENTS

| 8,486,049 | B2 * | 7/2013 | Guala | A61M 39/045 604/533 |
| 2008/0228172 | A1 * | 9/2008 | Petry | A61M 5/158 604/533 |
| 2010/0179514 | A1 | 7/2010 | Guala | |
| 2011/0282302 | A1 * | 11/2011 | Lopez | A61M 39/26 604/246 |

(Continued)

FOREIGN PATENT DOCUMENTS

| CN | 106659438 A | 5/2017 |
| CN | 213554740 U | 6/2021 |
| JP | 2015509815 A | 4/2015 |

*Primary Examiner* — Phillip A Gray
(74) *Attorney, Agent, or Firm* — Kirton McConkie; Whitney Blair; Kevin Stinger (57) ABSTRACT

A catheter assembly may include a catheter adapter. A body of the catheter adapter may include a distal end, a proximal end, and a lumen extending through the distal end and the proximal end. A catheter may extend distally from the distal end of the body. The catheter adapter may include a side port, which may extend outwardly from the body. The catheter assembly may include a valve disposed within the lumen. The valve may include a channel extending through the valve. The catheter assembly may include a cannula fixed within the side port and disposed within the channel. The cannula may include an opening, and the valve may be configured to compress to expose the opening from within the valve.

8 Claims, 8 Drawing Sheets

(56) References Cited

U.S. PATENT DOCUMENTS

| | | |
|---|---|---|
| 2013/0090607 A1 | 4/2013 | McKinnon et al. |
| 2016/0129235 A1 | 5/2016 | Ryan |

\* cited by examiner

CATHETER ASSEMBLY HAVING A SIDE PORT VALVE

RELATED APPLICATIONS

This application is a continuation of U.S. patent application Ser. No. 16/878,121, filed May 19, 2020, and entitled CATHETER ASSEMBLY HAVING A SIDE PORT VALVE, which claims the benefit of U.S. Provisional Patent Application No. 62/860,537, filed Jun. 12, 2019, and entitled CATHETER ASSEMBLY HAVING A SIDE PORT VALVE, which are incorporated herein in their entirety.

BACKGROUND

Catheters are generally used for parenteral nutrition, intravenous fluid replacement, and administering analgesics and antibiotics. Catheters are also used for blood draw. Catheters can be inserted at the bedside using sterile techniques and can remain in place for several weeks.

A common type catheter is an over-the-needle catheter. As its name implies, a catheter that is "over-the-needle" may be mounted over an introducer needle having a sharp distal tip. The sharp distal tip may be used to pierce skin and a vein of a patient. Insertion of the catheter into the vein may follow the piercing of the vein by the introducer needle. The introducer needle typically has the sharp distal tip to pierce skin and the vein of the patient with minimal resistance to minimize the pain to the patient.

The introducer needle is generally placed at a steep inclined angle with respect to a surface of the skin and a longitudinal dimension of the vein to be pierced to allow penetration through the skin and a wall of the vein. The introducer needle and the catheter are generally inserted with a bevel of the introducer needle facing away from the skin of the patient. After the tip of the introducer needle pierces the wall, the angle of the insertion is lowered to be able to slide the introducer needle and the catheter into the vein a distance sufficient to properly position the catheter in the vein. Once placement of the introducer needle within the vein has been confirmed, the user may temporarily occlude flow in the vein and withdraw the introducer needle, leaving the catheter in place for future fluid infusion and/or blood withdrawal.

The subject matter claimed herein is not limited to embodiments that solve any disadvantages or that operate only in environments such as those described above. Rather, this background is only provided to illustrate one example technology area where some implementations described herein may be practiced.

SUMMARY OF THE INVENTION

The present disclosure relates generally to a catheter assembly, as well as related devices, systems, and methods. In some embodiments, the catheter assembly may include a catheter adapter, which may include a body and a side port extending outwardly from the body. In some embodiments, the body may include a distal end, a proximal end, and a lumen extending through the distal end of the body and the proximal end of the body. In some embodiments, the side port may be disposed between the distal end and the proximal end. In some embodiments, the side port may include an outer opening.

In some embodiments, the catheter assembly may include a valve disposed within the side port. In some embodiments, the valve may include a channel extending through the valve. In some embodiments, the catheter assembly may include a cannula, which may be fixed within the side port. In some embodiments, the cannula may be disposed within the channel. In some embodiments, the cannula may include one or more openings. In some embodiments, the valve may be configured to compress to expose the openings from within the valve. In some embodiments, the catheter assembly may include a catheter extending distally from the distal end of the body. In some embodiments, the catheter assembly may include another valve, which may be generally cylindrical and/or disposed within the lumen.

In some embodiments, the side port and the body may be monolithically formed as a single unit. In some embodiments, the valve may be constructed of rubber or another suitable resilient material. In some embodiments, the valve may include a first end, a second end, and an accordion portion between the first end and the second end. In some embodiments, a diameter of the first end and a diameter of the second end may be greater than a diameter of the accordion portion. In some embodiments, the valve may include a rim and the side port may include a groove. In some embodiments, the rim may be disposed within the groove to secure the valve within the side port.

In some embodiments, the cannula may include a blunt, closed end. In some embodiments, the blunt, closed end of the cannula may seal an end of the channel, which may prevent bacteria from entering the catheter assembly. In further detail, in some embodiments, the blunt, closed end may include a first circumference and the end of the channel may include a second circumference approximately equal to the first circumference, which may facilitate a seal at the end of the channel.

In some embodiments, the openings may include a first opening, a second opening, and/or a third opening. In some embodiments, one or more of the first opening, the second opening, and the third opening may be spaced apart around a circumference of the cannula. In some embodiments, one or more of the first opening, the second opening, and the third opening may be proximate the blunt, closed end. In some embodiments, the cannula may include an annular body. In some embodiments, the first opening, the second opening, and/or the third opening may be disposed between the blunt, closed end of the cannula and the annular body.

In some embodiments, the catheter assembly may include a base, which may be fixed to the cannula. In some embodiments, the cannula may include an opening which may extend along a length of the cannula from the blunt, closed end to the base. In these and other embodiments, the blunt, closed end of the cannula may be semi-circular, and the end of the channel may be generally semi-cylindrical, which may facilitate a seal at the end of the channel. In some embodiments, the channel may be generally semi-cylindrical. In some embodiments, the base may include a hole, which may be aligned with the opening.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DESCRIPTION OF EMBODIMENTS

Referring now to FIGS. 1A-3E, a catheter assembly 10 may include a catheter adapter 12, which may include a body 14 and a side port 16 extending outwardly from the body 14. In some embodiments, the side port 16 and the body 14 may be monolithically formed as a single unit. In some embodiments, the body 14 may include a distal end 18, a proximal end 20, and a lumen 22 extending through the distal end 18 of the body 14 and the proximal end 20 of the body 14. In some embodiments, the side port 16 may be disposed between the distal end 18 and the proximal end 20. In some embodiments, the side port 16 may include an outer opening 24.

In some embodiments, the catheter assembly 10 may include a valve 26 disposed within the side port 16. In some embodiments, the valve 26 may be constructed of rubber or another suitable resilient material. In some embodiments, the valve 26 may include a channel 27 extending through the valve 26. In some embodiments, the catheter assembly 10 may include a cannula 28. In some embodiments, the cannula 28 may be disposed within the channel 27. In some embodiments, the cannula 28 may include a blunt, closed end 30.

In some embodiments, the catheter assembly 10 may include a catheter 32 extending distally from the distal end 18 of the body 14. In some embodiments, the catheter 32 may include a peripheral intravenous catheter ("PIVC"), a peripherally inserted central catheter ("PICC"), a midline catheter, or another suitable catheter. In some embodiments, a needle assembly that includes an introducer needle 33 may extend through the catheter adapter 12, as illustrated, for example, in FIG. 1A. In some embodiments, in response to the introducer needle 33 and catheter 32 being inserted into vasculature of a patient, the needle assembly may be removed from the catheter adapter 12, as illustrated, for example, in FIG. 1B. In some embodiments, a blood collection device may be coupled to the catheter adapter 12, and when the catheter 32 is inserted into the vasculature of the patient, blood may flow from the vasculature, distally through the catheter 32, through the catheter adapter 12, and into the blood collection device.

Figure 1A:
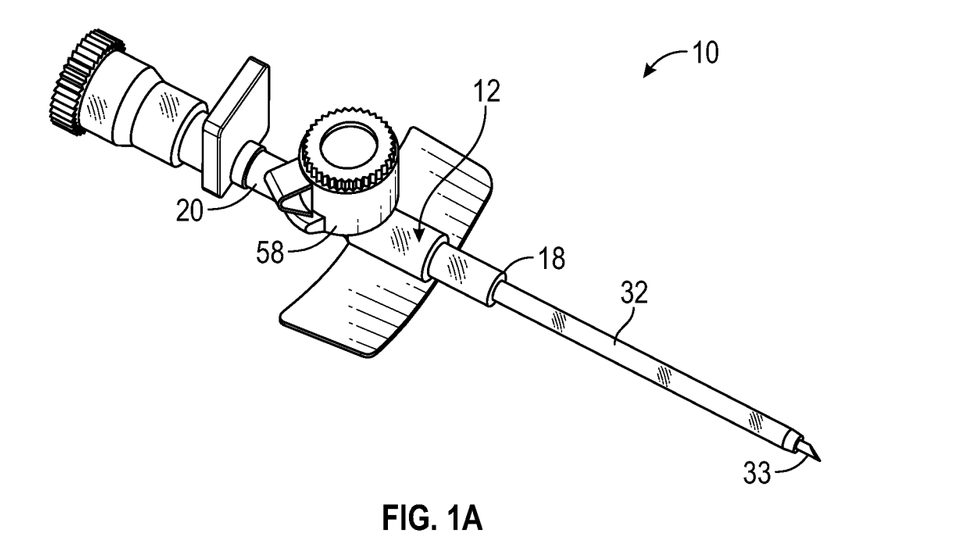
FIG. 1A is an upper perspective view of a catheter assembly, according to some embodiments.
Figure 1B:
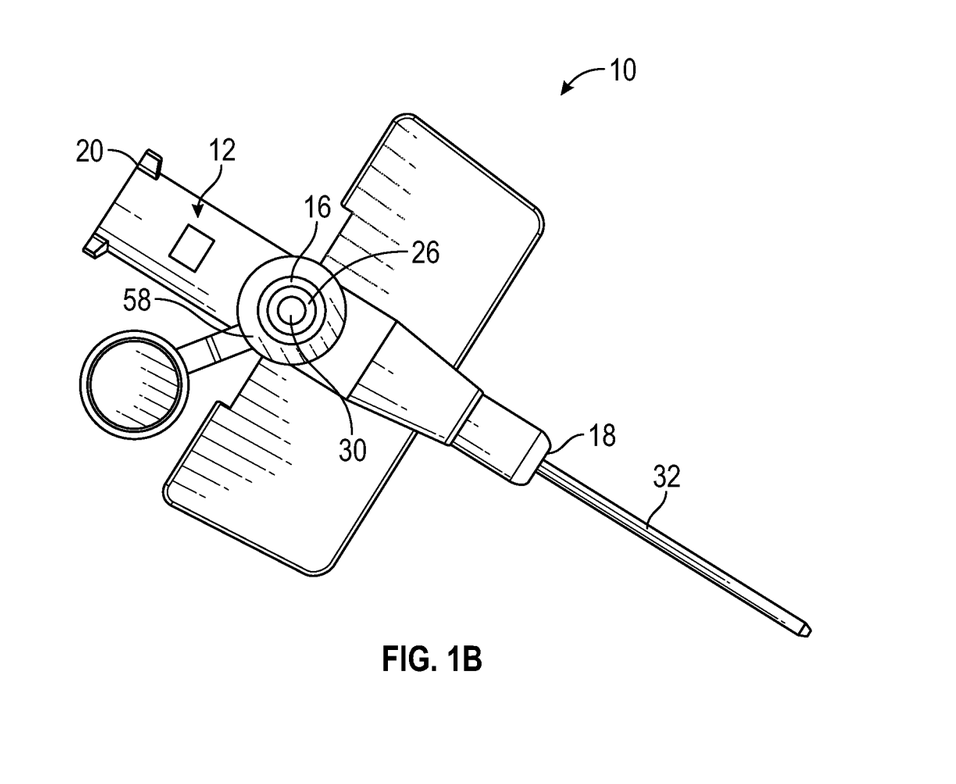
FIG. 1B is a top view of the catheter assembly, illustrating an example cap opened.
Figure 2A:
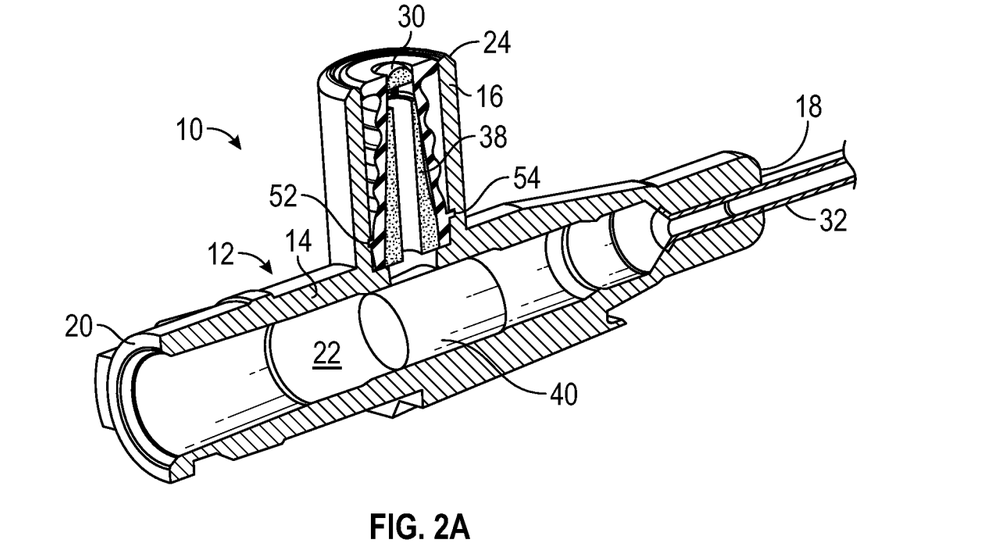
FIG. 2A is a partial cutaway view of the catheter assembly, according to some embodiments.
Figure 2B:
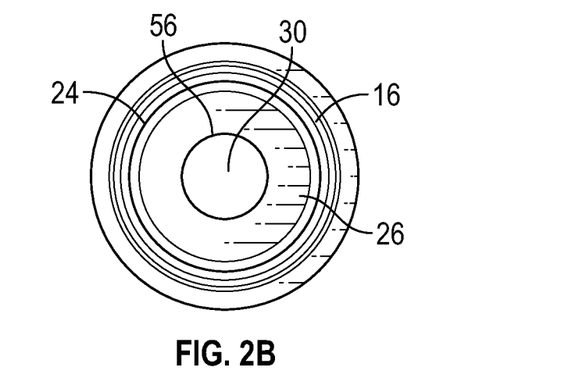
FIG. 2B is a top view of an example side port of the catheter assembly, according to some embodiments.
Figure 2C:
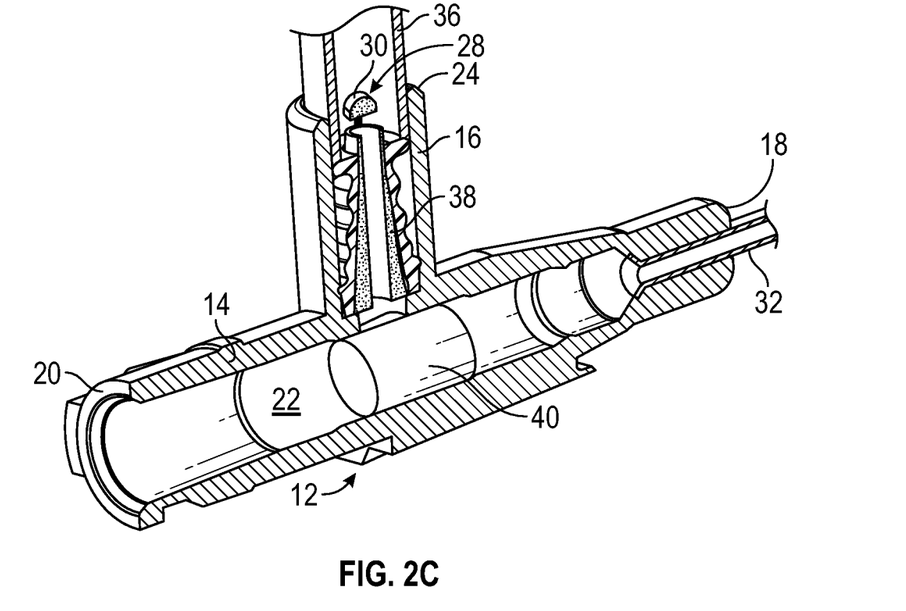
FIG. 2C is a partial cutaway view of the catheter assembly, illustrating an example medical device inserted into the side port to compress an example valve, according to some embodiments.
Figure 3A:
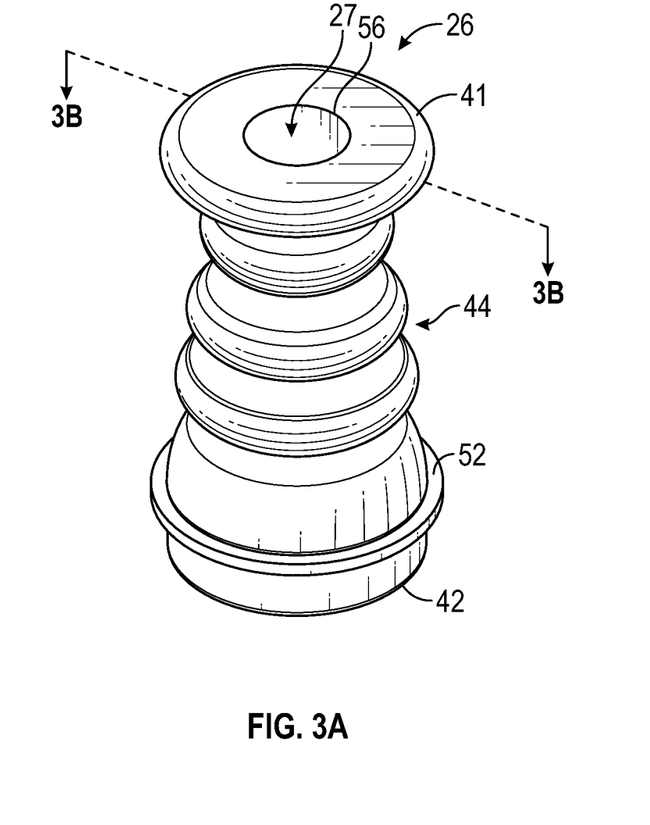
FIG. 3A is an upper perspective view of the valve of the catheter assembly, according to some embodiments.
Figure 3B:
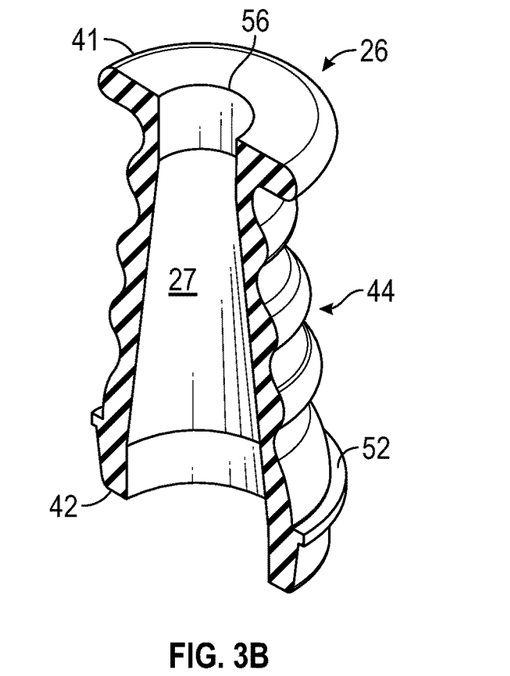
FIG. 3B is a cross-sectional view of the valve, according to some embodiments.
Figure 3C:
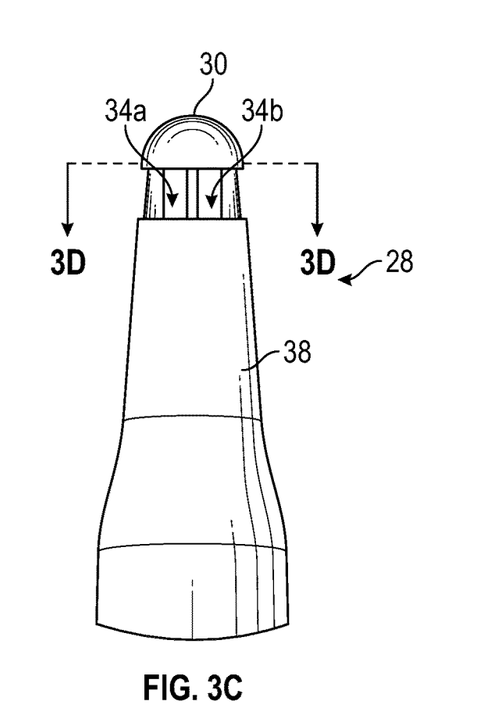
FIG. 3C is an upper perspective view of an example cannula of the catheter assembly, according to some embodiments.
Figure 3D:
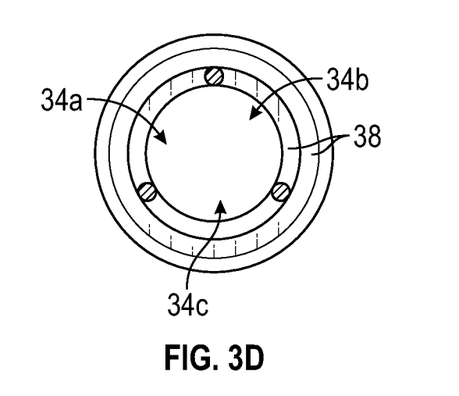
FIG. 3D is a cross-sectional view of the cannula along the line 3D-3D of FIG. 3C, according to some embodiments.
Figure 3E:
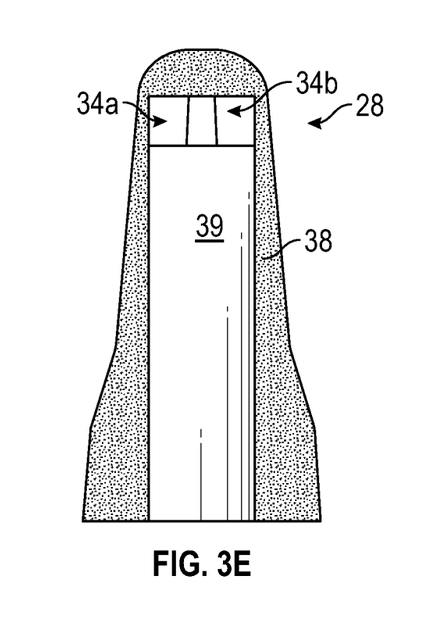
FIG. 3E is another cross-sectional view of the cannula, according to some embodiments.
Figure 4A:
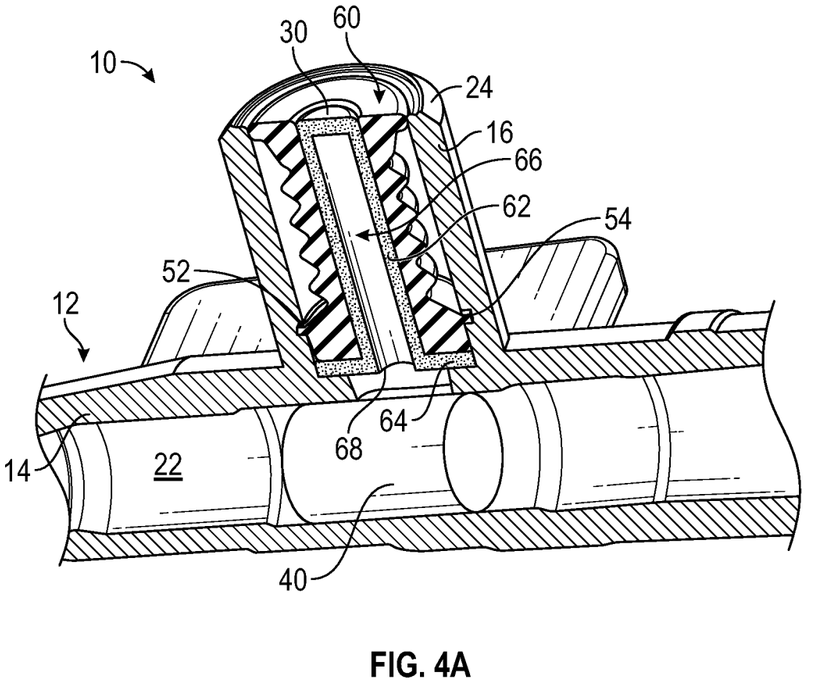
FIG. 4A is a cross-sectional view of the catheter assembly, illustrating another example cannula and another example valve, according to some embodiments.
Figure 4B:
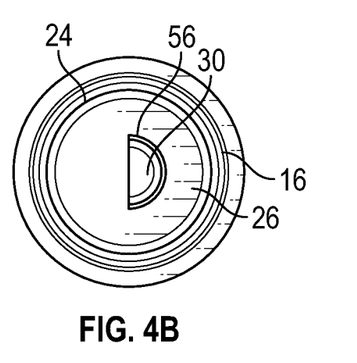
FIG. 4B is a top view of the side port of the catheter assembly, according to some embodiments.
Figure 4C:
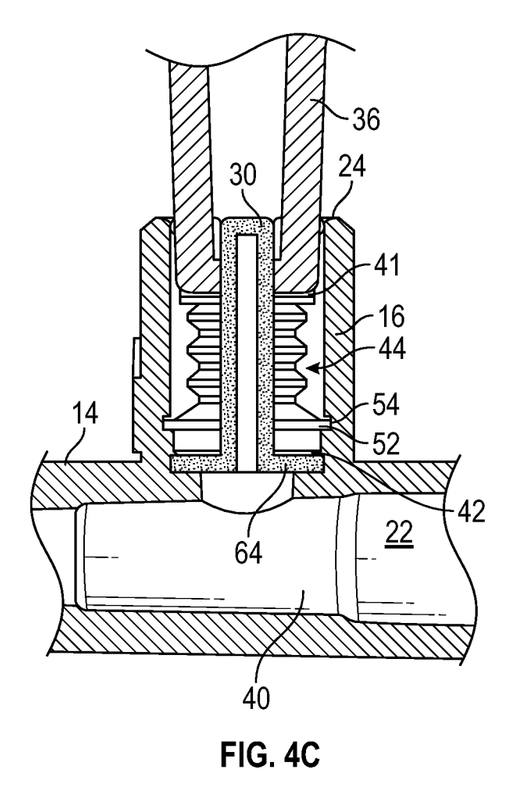
FIG. 4C is a cross-sectional view of the catheter assembly, illustrating the medical device inserted into the side port to compress the other valve, according to some embodiments.
Figure 5A:
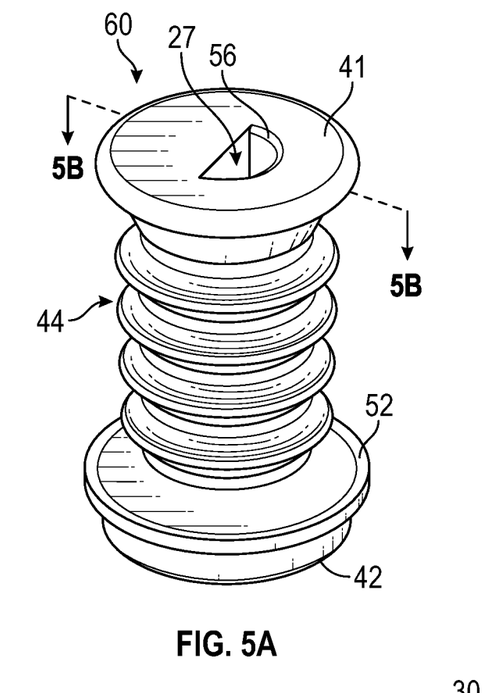
FIG. 5A is an upper perspective view of the other valve, according to some embodiments.
Figure 5B:
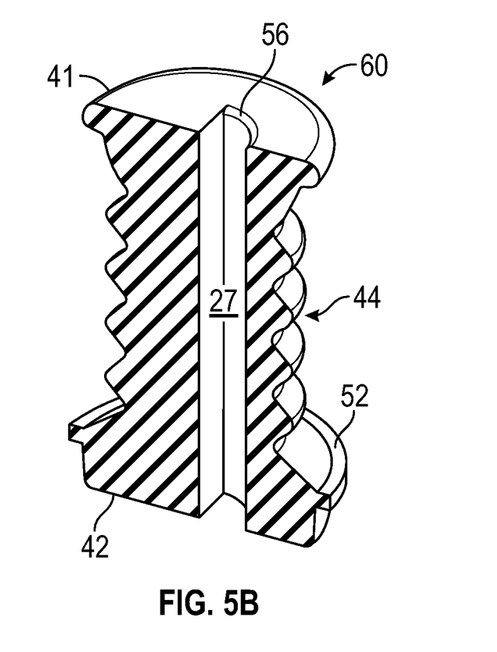
FIG. 5B is a cross-sectional view of the other valve, according to some embodiments.
Figure 5C:
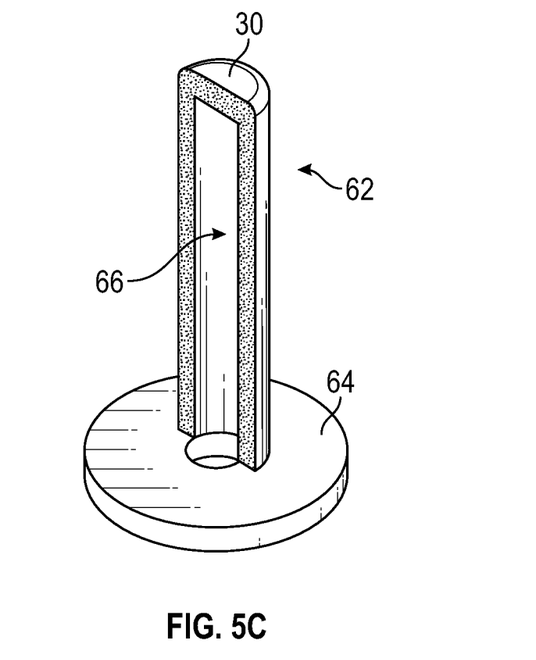
FIG. 5C is an upper perspective view of the other cannula, according to some embodiments.

In some embodiments, the cannula 28 may include one or more openings 34. As illustrated in FIG. 2C, in some embodiments, the valve 26 may be configured to compress to expose the openings 34 from within the valve 26. In some embodiments, a medical device 36 may be inserted into and/or coupled to the side port 16, which may compress the valve 26 to expose the openings 34 from within the valve 26 and allow fluid to flow from the medical device 36, through the openings 34, through an annular body 38 of the cannula 28. In some embodiments, in response to the medical device 36 being removed and/or uncoupled from the side port 16, the valve 26 may resiliently return to a position in which the openings 34 are within the valve 26.

In some embodiments, the openings 34 may include a first opening 34a, a second opening 34b, and/or a third opening 34c (which may be referred to collectively in the present disclosure as "openings"). In some embodiments, the openings 34 may include more than three openings or only one opening. In some embodiments, one or more of the openings 34 may be spaced apart around a circumference of the cannula 28, as illustrated in Figure. In these embodiments, the openings 34 may be aligned with each other.

In some embodiments, one or more of the openings 34 may be proximate the blunt, closed end 30. In some embodiments, one or more of the openings 34 may be disposed between the blunt, closed end 30 of the cannula 28 and the annular body 38. In some embodiments, the annular body 38 may include a fluid pathway 39 or channel extending through the annular body 38. In some embodiments, the openings 34 may be in fluid communication with the fluid pathway 39. In some embodiments, the openings 34 may be spaced apart from each other by beams or separators, which may extend between the blunt, closed end 30 and the annular body 38. In some embodiments, the beams or separators may be monolithically formed with the blunt, closed end 30 and/or the annular body 38 as a single unit.

In some embodiments, the catheter assembly 10 may include another valve 40, which may be generally cylindrical and/or disposed within the lumen. In some embodiments, the other valve 40 may be solid or may include a channel extending there through and aligned with a longitudinal axis of the body. In some embodiments, the side port 16 may be generally perpendicular with respect to the body 14, which may facilitate fluid from the medical device 36 contacting the other valve 40 at about a 90° angle, which may facilitate operation and opening of the other valve 40. In some embodiments, the other valve 40 may open to allow fluid communication between the side port 16 and the lumen 22. In some embodiments, the other valve 40 may open when a portion of the other valve 40 is depressed in response to contact by the fluid. In some embodiments, the other valve 40 may include any suitable valve, which may be generally perpendicular to the valve 26.

In some embodiments, the valve 26 may include a first end 41, a second end 42, and an accordion portion 44 between the first end 41 and the second end 42. In some embodiments, a diameter of the first end 41 and a diameter of the second end 42 may be greater than a diameter of the accordion portion 44. In some embodiments, an outer surface of the accordion portion 44 may be curved.

In some embodiments, the cannula 28 may be fixed within the side port 16. As an example, the cannula 28 may be fixed to the side port and/or the catheter adapter 12. As another example, the valve 26 may be coupled to the side port 16, and the cannula 28 may fit snugly within the valve 26. In some embodiments, an end of the cannula 28 opposite the blunt, closed end 30 may have a diameter greater than an end 56 of the channel 27 prior to and/or after insertion of the medical device 36, which may facilitate the cannula 28 being secured within the valve 26. In some embodiments, the end of the cannula 28 opposite the blunt, closed end 30 may contact and/or be secured to a stepped surface, which may facilitate securement of the cannula 28 within the side port 16.

In some embodiments, the valve 26 may be coupled to the catheter adapter 12 in any number of suitable ways. In some embodiments, the valve 26 may include a rim 52, and the side port 16 may include a groove 54. In some embodiments, the rim 52 may be disposed within the groove 54 to secure the valve 26 within the side port 16. In some embodiments, the rim 52 and/or the groove 54 may be annular.

In some embodiments, the blunt, closed end 30 of the cannula 28 may seal the end 56 of the channel 27, which may prevent bacteria from entering the catheter assembly 10. In further detail, in some embodiments, the blunt, closed end 30 may include a first circumference and the end 56 of the channel 27 may include a second circumference approximately equal to the first circumference, which may facilitate a seal at the end 56 of the channel 27. In some embodiments, the catheter assembly 10 may not include a cap 58 because the blunt, closed end 30 and the valve 26 may seal the catheter adapter 12 from the external environment.

Referring now to FIGS. 4A-5C, in some embodiments, the catheter assembly 10 may include a valve 60 and a cannula 62. In some embodiments, the valve 60 may include or correspond to the valve 26 described with respect to FIGS. 1A-3E and/or the cannula 62 may include or correspond to the cannula 28 described with respect to FIGS. 1A-3E. In some embodiments, the valve 60 may include one or more features of the valve 26 described with respect to FIGS. 1A-3E and/or the cannula 62 may one or more features of the cannula 28 described with respect to FIGS. 1A-3E.

In some embodiments, the catheter assembly 10 may include a base 64, which may be fixed to the cannula 28. In some embodiments, the cannula 28 and the base 62 may be monolithically formed as a single unit. In some embodiments, the cannula 28 may include an opening 66 which may extend along a length of the cannula 28. In some embodiments, the cannula 28 may include an opening 66 which may extend along a length of the cannula 28 from the blunt, closed end 30 to the base 64. In these and other embodiments, the blunt, closed end 30 of the cannula 28 may be semi-circular, and the end 56 of the channel 27 may be generally semi-cylindrical, which may facilitate a seal at the end 56 of the channel 27. In some embodiments, the channel 27 may be generally semi-cylindrical. In some embodiments, the base 64 may include a hole 68, which may be aligned with the opening 66.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter assembly, comprising:
    a catheter adapter, comprising:
        a body, comprising a distal end, a proximal end, and a lumen extending through the distal end and the proximal end; and
        a side port extending outwardly from the body and disposed between the distal end and the proximal end, wherein the side port comprises an outer opening;
    a valve disposed within the side port, wherein the valve comprises a channel extending through the valve, wherein the channel is semi-cylindrical;
    a cannula fixed within the side port and disposed within the channel, wherein the cannula comprises an opening, wherein the opening is within the valve when the valve is in a first position, wherein the valve is configured to compress to a second position in which the valve is below the opening and the opening is exposed from within the valve, wherein the cannula further comprises an open end and a closed end opposite the open end;
    a base fixed to the cannula and extending outwardly from the cannula, wherein the open end is proximate a hole within the base, wherein the cannula is formed by a semi-cylindrical wall and the closed end is semi-circular such that the closed end is configured to seal the channel when the valve is in the first position, wherein the opening extends from the base to the closed end and through the wall forming the cannula; and
    a catheter extending distally from the distal end of the body.

2. The catheter assembly of claim 1, wherein the side port and the body are monolithically formed as a single unit.

3. The catheter assembly of claim 2, wherein the catheter assembly further comprises another valve, wherein the other valve is generally cylindrical and disposed within the lumen.

4. The catheter assembly of claim 2, wherein the valve is constructed of rubber.

5. The catheter assembly of claim 4, wherein the valve comprises a first end, a second end, and an accordion portion between the first end and the second end.

6. The catheter assembly of claim 5, wherein a diameter of the first end and a diameter of the second end are greater than a diameter of the accordion portion.

7. The catheter assembly of claim 6, wherein the valve further comprises a rim, wherein the side port comprises a groove, wherein the rim is disposed within the groove to secure the valve within the side port.

8. The catheter assembly of claim 1, wherein the closed end is blunt.

* * * * *